United States Patent [19]

Ishida et al.

[11] Patent Number: 5,141,741

[45] Date of Patent: Aug. 25, 1992

[54] ANTI-SUNBURN SKIN-CARE PREPARATION

[75] Inventors: Keiichiro Ishida; Yoshimi Sato, both of Tokyo; Makoto Egawa, Inzai; Keiji Takeuchi, Tokyo, all of Japan

[73] Assignee: Lion Corporation, Tokyo, Japan

[21] Appl. No.: 444,960

[22] Filed: Dec. 4, 1989

[30] Foreign Application Priority Data

Dec. 9, 1988 [JP] Japan .................. 63-311401

[51] Int. Cl.$^5$ .............. A61K 7/02; A61K 7/021; A61K 7/42; A61K 7/46; A61K 7/48

[52] U.S. Cl. ................ 424/59; 424/DIG. 5; 424/60; 424/63; 424/64; 424/69; 512/4; 514/772; 514/773; 514/777; 514/778; 514/779; 514/782; 514/783; 514/784; 514/785; 514/786; 514/787; 514/788; 514/844; 514/845; 514/846; 514/847; 514/873; 514/904

[58] Field of Search ............................. 424/59

[56] References Cited

PUBLICATIONS

Chem. Abs., 1983, vol. 100, 79562z.
Chem. Abs., 1984, vol. 102, 31905c.

Primary Examiner—Dale R. Ore
Attorney, Agent, or Firm—Hopgood, Calimafde, Kalil, Blaustein & Judlowe

[57] ABSTRACT

A novel anti-sunburn skin-care preparation, such as creams, foundations, milky lotions and the like, is proposed which contains, as the ultraviolet-absorbing and -shielding ingredient, a salt of ellagic acid with a polyvalent metal, e.g., calcium, barium and magnesium. The skin-care preparation is free from the problem of irritation and sensitization of human skin and exhibits excellent anti-sunburn effect with durability.

9 Claims, No Drawings

ANTI-SUNBURN SKIN-CARE PREPARATION

BACKGROUND OF THE INVENTION

The present invention relates to a novel anti-sunburn skin-care preparation or, more particularly, to an anti-sunburn skin-care preparation formulated with a specific organic compound having strong absorption of ultraviolet light, hereinafter referred to as UV light, but never used as an ingredient of skin-care preparations, which compound is very effective lastingly in the sunburn-preventing effect without the problems of irritation to or sensitization of human skin. The invention also relates to a method for the protection of human skin from sunburn when the skin is exposed to UV light.

Needless to say, the wavelength region of the sun light covers the ultraviolet range which can be divided into three sub ranges including the long-wavelength UV light having a wavelength in the range from about 320 to about 400 nm, referred to as the UV-A light hereinbelow, medium-wavelength UV light having a wavelength in the range from about 280 to about 320 nm, referred to as the UV-B light hereinbelow, and short wavelength UV light having a wavelength shorter than about 280 nm, referred to as the UV C light hereinbelow.

It is known that the UV-B light, among the three types of UV light mentioned above, is responsible for acute inflammation or erythema and burn on the human skin exposed to the light and the UV A light directly causes suntan in the human skin by the oxidation of the reduced melanin in the cuticle. On the other hand, the UV-C light, which is absorbed almost completely in the atmospheric air so that the intensity of the UV-C light arriving at the earth's surface is very low, is believed to be even more harmful against human skin than the UV-B light.

In view of the above described characteristic influences of the UV lights, most of conventional skin-care preparations for sunburn prevention are formulated with an UV absorber capable of absorbing mainly the UV-8 light having the strongest activity to cause skin inflammation, such as benzophenone compounds and the like, preventing the UV-B light from reaching the skin. It is also conventional that a skin-care preparation is compounded with a fine inorganic powder either alone or in combination with the above mentioned UV absorber with an object to shield the UV lights by scattering before the light reaches the human skin.

Anti-sunburn skin-care preparations compounded with an inorganic powder as an UV scattering agent, however, are not always quite satisfactory because of the problems of poor or uneven finishing of make-up and collapsing of the make-up in part to cause inadvertent sunburn at the spots.

On the other hand, results of the dermatological studies obtained in recent years in relation to the influences of UV lights indicate that the UV-A light also has various adverse effects on the human skin exposed thereto such as the phototoxic reactions induced by the exposure to the light, acceleration of the peroxidation of squalene contained in the skin and promoted aging of the human skin. It is also indicated that the UV-A light penetrates the human skin more deeply than the Uv-B light.

Accordingly, it is desired to formulate an anti-sunburn skin care preparation with an UV absorber having excellent absorptivity for the UV-A light. Several compounds have been proposed as a UV A light absorber including 4-(1,1-dimethylethyl)-4'-methoxy dibenzoyl methane disclosed in Japanese Patent Kokai 55-66535, specific benzophenone derivatives disclosed in Japanese Patent Kokai 62-138422 and the like.

The above described UV absorbers conventionally formulated in anti-sunburn skin-care preparations in general have a problem relative to the safety against human body and the sustainability of the anti-sunburn effect because these compounds are soluble in water, organic solvents, oleaginous materials, sebaceous matters and the like to be absorbed percutaneously or to be diffused over the skin surface.

SUMMARY OF THE INVENTION

The present invention has an object to provide, by overcoming the above described problems and disadvantages in the conventional anti-sunburn skin-care preparations, a novel UV-absorbing compound and an improved anti-sunburn skin-care preparation capable of exhibiting excellent anti-sunburn effects with sustainability and free from the problem of irritativeness against the human skin in addition to the satisfactory feeling of usability and acceptable finishing when the preparation is used for make-up.

Thus, the anti-sunburn skin-care preparation of the invention comprises, as an effective ingredient for the absorption of ultraviolet light, from 0.01 to 10% by weight of a polyvalent metal salt of an ellagic acid compound represented by the general formula

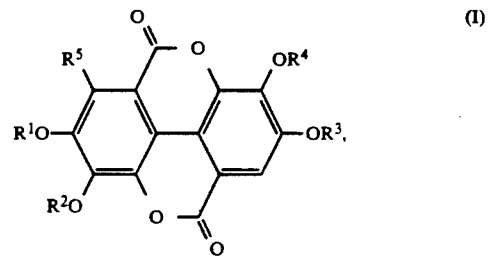

in which $R^1$, $R^2$, $R^3$ and $R^4$ are, each independently from the others, a hydrogen atom, an alkyl group having 1 to 20 carbon atoms, an acyl group having 1 to 20 carbon atoms, a polyoxyalkylene group of the formula

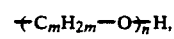

m being 2 or 3 and n being a positive integer, or a saccharide residue expressed by the formula

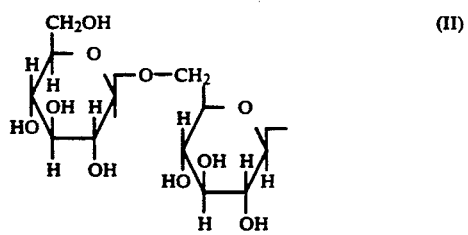

and $R^5$ is a hydrogen atom, a hydroxy group or an alkoxy group having 1 to 8 carbon atoms, and a cosmetic carrier. The polyvalent metal salt of the ellagic acid compound is a novel compound not known in the prior art nor described in any literatures.

The invention also has an object to prevent sunburn on the human skin by applying thereto the above described novel skin-care preparation.

DETAILED DESCRIPTION OF THE PREFERRED EMBODIMENTS

In view of the above described problems and disadvantages in the UV absorbers conventionally formulated in anti-sunburn skin-care preparations in the prior art, the inventors have conducted extensive investigations to discover a novel UV absorber compound and to develop an anti-sunburn skin-care preparation with the above mentioned object and, as a result, have arrived at an unexpected discovery that the above defined specific ellagic acid derivative in the form of a polyvalent metal salt has an excellent UV absorbing and shielding power and still has little adverse influences against human skin such as irritation and sensitization and that a skin-care preparation compounded therewith exhibits excellent anti-sunburn effects with sustainability in addition to the acceptable feeling of usability and finishing condition when the preparation is used for make-up leading to completion of the present invention.

As is described above, the most characteristic feature of the inventive anti-sunburn skin-care preparation is the formulation of the specific ellagic acid derivative defined above. The ellagic acid derivative is a polyvalent metal salt of an ellagic acid compound represented by the general formula (I), in which $R^1$, $R^2$, $R^3$ and $R^4$ are, each independently from the others, a hydrogen atom, an alkyl group having 1 to 20 carbon atoms, an acyl group having 1 to 20 carbon atoms, a polyoxyalkylene group of the formula

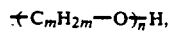

m being 2 or 3 and n being a positive integer, or a saccharide residue expressed by the formula (II), and $R^5$ is a hydrogen atom, a hydroxy group or an alkoxy group having 1 to 8 carbon atoms, e.g., preferably, methoxy and ethoxy groups. Preferably, the ellagic acid compound is ellagic acid which is a compound of the formula (I) in which each of the symbols $R^1$ to $R^5$ denotes a hydrogen atom. It is of course preferable with an object to increase the oleophilicity or to modify the hydrophilicity of the compound by introducing a long-chain alkyl group as one or more of the groups denoted by the symbols $R^1$ to $R^5$.

Examples of the particular ellagic acid compounds include: ellagic acid; 3,4-di-O-methyl ellagic acid; 3,3'-di-O-methyl ellagic acid; 3,3', 4-tri-O-methyl ellagic acid; 3 methyl-4-methyl-5-hydroxy ellagic acid; amritoside; and the like. These ellagic acid compounds are contained in and can be extracted from various kinds of plants including *Eucalyptus cortex, Cinips gallae tinctoriae, Geranium herba* and the like according to the method disclosed, for example, in Japanese Patent Publication 53-14605.

The ellagic acid compound is used in the inventive skin-care preparation in the form of a salt with a polyvalent metal, i.e. a metal of divalency or higher valency. The polyvalent metal suitable for the purpose include copper belonging to the Ib Group, calcium, strontium, barium and magnesium belonging to the IIa Group, zinc belonging to the IIb Group, aluminum belonging to the IIIb Group, titanium and zirconium belonging to the IVa Group and iron and cobalt belonging to the VIII Group of the Periodic Table, of which the alkaline earth metals such as calcium, strontium, barium and magnesium are preferred.

The polyvalent metal salt of the ellagic acid derivative can be prepared easily from a water-soluble salt of these metals. Thus, an ellagic acid derivative of the formula (I) given above is dissolved in an aqueous alkaline solution in a concentration in the range from 0.1 to 50% by weight and this aqueous solution of the alkali metal salt of the acid is admixed gradually under agitation with an aqueous solution containing a water-soluble salt of the polyvalent metal, preferably, in a concentration of 0.1 to 50% by weight so that the polyvalent metal salt of the acid is precipitated. The pH value of the aqueous solution is gradually decreased by the addition of the solution of the polyvalent metal salt while the PH value of the solution should be kept in a range of 12 to 13 by concurrently adding an aqueous alkali solution after a moment when the PH value of the solution has dropped to 12 by the addition of the salt solution. Agitation of the solution is continued for further 20 minutes to 2 hours after completion of the addition of the salt solution and the alkali solution to complete the reaction. Suitable water-soluble polyvalent metal salts include chlorides, nitrates, sulfates and acetates of zinc, calcium, barium, magnesium, aluminum and the like.

The precipitates of the polyvalent metal salt of the acid are collected by a suitable method of solid-liquid separation such as filtration and centrifugal separation and thoroughly washed with water to be freed from the mother liquor and the hydroxide of the polyvalent metal followed by drying to give the desired polyvalent metal salt of the ellagic acid derivative in a high purity.

The polyvalent metal salt of the ellagic acid derivative is obtained in this manner in the form of a yellow to yellowish brown odorless powder which is insoluble in water, alcohol, oils and fats and the like though dispersible therein. Accordingly, the salt can be compounded in a skin-care preparation in the form of a dispersion in ethyl alcohol, oils and fats and the like.

The polyvalent metal salt of the ellagic acid derivative has high absorptivity to the UV-B light which is responsible for acute inflammation or erythema of the human skin exposed to the sun light. The salt also has higher than medium absorptivity to the UV-A light which is responsible for the direct suntan of the human skin by the oxidation of the reduced melanin in the cuticle.

It is already established that the ellagic acid derivatives used as a starting material of the polyvalent metal salt have no particular problems relative to the acute toxicity, skin irritativeness, skin sensitization, mutagenicity and the like in the practical application to the human skin with high safety. The polyvalent metal salts are also free from irritation and sensitization of human skin according to the results of the application tests.

The polyvalent metal salts of the ellagic acid derivative are compounded, either singly or as a combination of two kinds or more according to need, in a skin-care preparation in an amount of, usually, 0.01 to 10% by weight or, preferably, 0.05 to 5% by weight based on the overall amount of the preparation. Various ingredients in conventional skin-care preparations have no particular reactivity with the ellagic acid compound and can be used without limitations including not only water, oleaginous matters and surface active agents but also other additives such as moisturizers, lower alcohols, thickeners, antioxidants, chelating agents, pH-controlling agents, antiseptics, perfumes, coloring agents, conventional UV absorbers, UV scattering agents, vitamins, amino acids and the like. Usable oleaginous materials include oils and fats such as olive oil, jojoba oil, castor oil, cacao butter, camellia oil, coconut oil, Japan tallow, grape-seed oil, avocado oil, mink oil, yolk oil, hardened oils and the like, waxes such as whale wax, beeswax, lanolin, carnauba wax, candelilla wax and the like, hydrocarbon compounds such as liquid paraffin, ceresine, squalane, microcrystalline wax, paraffin wax, petrolatum and the like, higher fatty acids such as stearic acid, oleic acid, lauric acid, myristic acid, isostearic acid behenic acid and the like, higher alcohols such as cetyl alcohol, stearyl alcohol, lanolin alcohol, 2-octyl dodecanol, 2-hexyl decanol and the like and esters of higher fatty acids such as isopropyl myristate, butyl stearate, isopropyl palmitate, 2-octyldodecyl myristate, 2-octyldodecyl oleate, cholesterol oleate and the like. Usable surface active agents include anionic surface active agents such as sodium stearate, sodium cetyl sulfate, polyoxyethylene lauryl ether phosphate, sodium lauryl phosphate, triethanolamine palmitate, sodium n-acyl glutamates and the like, cationic surface active agents such as stearyl dimethyl benzyl ammonium chloride, stearyl trimethyl ammonium chloride and the like, amphoteric surface active agents such as alkyl aminoethyl glycine hydrochloride and the like and non-ionic surface active agents such as glycerin monostearate, sorbitan monostearate, fatty acid esters of sucrose, propylene glycol monostearate, polyoxyethylene oleyl ether, polyoxyethylene glycol monostearate, polyoxyethylene sorbitan monopalmitate, polyoxyethylene coconut oil fatty acid ester monoethanolamide, polyoxyethylene-polyoxypropylene glycols, polyoxyethylene castor oil ester, polyoxyethylene lanolin and the like. Usable moisturizers include polyhydric alcohols such as glycerin, 1,3-butylene glycol, propylene glycol, sorbitol, polyethylene glycol, dipropylene glycol and the like, NMF (natural moisturizing factor) materials such as amino acids, sodium lactate, sodium pyrrolidone carboxylate and the like and water-soluble polymeric materials such as hyaluronic acid, collagen, mucopolysaccharides, chondroitin sulfate and the like. Usable lower alcohols include ethyl alcohol, isopropyl alcohol and the like. Usable thickeners include naturally-occurring polymeric materials such as sodium alginate, xanthan gum, aluminum silicate, quince seed extract, tragacanth gum, starch and the like, semi-synthetic polymeric materials such as methyl cellulose, hydroxyethyl cellulose, carboxymethyl cellulose, soluble starch, cationated cellulose and the like and synthetic polymeric materials such as carboxyvinyl polymers, polyvinyl alcohol and the like. Usable antioxidants include dibutyl hydroxytoluene, butyl hydroxy anisole, propyl gallate, ascorbic acid and the like. Usable chelating agents include disodium ethylenediamine tetraacetate, ethane hydroxy diphosphate, pyrophosphates, hexametaphosphates, citric acid, tartaric acid, gluconic acid and the like. Usable pH-controlling agents include sodium hydroxide, triethanol amine, citric acid, sodium citrate, boric acid, borax, sodium hydrogen phosphate and the like. Usable antiseptics include methyl 4-hydroxybenzoate, ethyl 4-hydroxybenzoate, dehydroacetic acid, salicylic acid, sorbic acid, benzoic acid, benzalkonium chloride and the like. Usable vitamins include vitamin A, vitamin B, vitamin C, vitamin D, vitamin E, vitamin F, vitamin K, vitamin P, vitamin U, carnitine, ferulic acid, γ-oryzanol, α-lipoic acid, orotic acid and derivatives thereof and the like. Usable amino acids include glycine, alanine, valine, leucine, isoleucine, serine, threonine, phenylalanine, tyrosine, tryptophan, cystine, methionine, proline, hydroxyproline, arginine, hystidine and lysine as well as derivatives thereof. Although the skin-care preparations compounded with the ellagic acid compound exhibit a sufficiently high sunburn-preventing effect, it is optional that the preparation is further compounded with a conventional UV absorber such as 2-hydroxy-4-methoxy benzophenone, octyl dimethyl 4-aminobenzoate, ethylhexyl 4-methoxy cinnamate and the like and/or UV scatterinq agent such as titanium dioxide, kaolin talc and the like. Any conventional additives other than the above mentioned ones can optionally be admixed each in a limited amount according to need.

The inventive anti-sunburn skin-care preparation can be prepared in any desired form including vanishing and cold creams, milky lotions, toilet waters, beauty lotions, packs, face powders, lip creams, lipsticks, under-make-ups, foundations, bath liquids and the like.

In the following, examples are given to illustrate the invention in more detail but not to limit the scope of the invention in any way.

In the following, the term of "parts" always refers to "parts by weight".

PREPARATION EXAMPLE 1

Into an aqueous dispersion of 30.0 g of ellagic acid in 500 g of purified water under agitation were gradually added 500 g of a 1N aqueous solution of sodium hydroxide so that the ellagic acid was completely dissolved to give an aqueous solution of sodium ellagate, into which a 20% aqueous solution of calcium chloride was added gradually under agitation. Precipitates were formed in the solution and the pH value of the solution was gradually decreased as the calcium chloride solution was added. When the pH value of the solution had reached 12, concurrent addition of a 1N aqueous solution of sodium hydroxide was started together with the calcium chloride solution so as to keep the pH value in the range from 12 to 13 until the overall added volume of the calcium chloride solution reached 1000 ml. Thereafter, agitation of the solution was continued for additional 2 hours to complete precipitation of the calcium salt. The precipitates were collected by centrifugation at 8000 rpm for 15 minutes and washed with water and ethyl alcohol followed by drying to give 35.2 g of calcium ellagate.

PREPARATION EXAMPLE 2

The experimental procedure was substantially the same as in Preparation Example 1 excepting replacement of 1000 ml of the 20% aqueous solution of calcium chloride with 1500 ml of a 15% aqueous solution of magnesium acetate to give 36.0 g of magnesium ellagate.

PREPARATION EXAMPLE 3

Into an aqueous dispersion of 5.0 g of ellagic acid in 100 g of purified water under agitation were gradually added 100 ml of a 1N aqueous solution of potassium hydroxide so that the ellagic acid was completely dissolved to give an aqueous solution of potassium ellagate, into which a 10% aqueous solution of barium chloride was added gradually under agitation. Precipitates were formed in the solution and the pH value of the solution was gradually decreased as the barium chloride solution was added. When the pH value of the solution had reached 12, concurrent addition of a 1N aqueous solution of potassium hydroxide was started together with the barium chloride solution so as to keep the pH value in the range from 12 to 13 until the overall added volume of the barium chloride solution reached 300 ml. Thereafter, agitation of the solution was continued for additional 30 minutes to complete precipitation of the barium salt. The precipitates were collected by filtration and washed with water and ethyl alcohol followed by drying to give 6.1 g of barium ellagate.

PREPARATION EXAMPLE 4

The experimental procedure was substantially the same as in Preparation Example 3 excepting replacement of 5.0 g of ellagic acid with 6.0 g of 3,4 di-O-methyl ellagic acid and 10% aqueous solution of barium chloride with 500 ml of a 5.0% aqueous solution of calcium acetate to give 6.5 g of calcium 3,4-di-O-methyl ellagate.

Measurement of Ultraviolet Absorption of the Ellagic Acid Salts

Each a 5 mg portion of the ellagic acid compounds prepared in Preparation Examples 1 to 4 described above was added to 50 ml of ethyl alcohol and dispersed therein by the ultrasonic irradiation for 10 minutes and the UV absorption of the thus obtained dispersion in ethyl alcohol was measured immediately thereafter to give the results shown below by the absorbance.

| Compound prepared in Preparation Example | Wavelength, nm | | | | | | |
|---|---|---|---|---|---|---|---|
| | 280 | 300 | 320 | 340 | 360 | 380 | 400 |
| 1 | 1.267 | 0.876 | 0.655 | 0.673 | 0.950 | 0.718 | 0.634 |
| 2 | 1.189 | 0.789 | 0.613 | 0.626 | 0.884 | 0.614 | 0.486 |
| 3 | 1.048 | 0.793 | 0.595 | 0.600 | 0.848 | 0.603 | 0.472 |
| 4 | 1.120 | 0.880 | 0.623 | 0.644 | 0.867 | 0.695 | 0.642 |

EXAMPLES 1 and 2 AND COMPARATIVE EXAMPLES 1 and 2

A skin-care cream composition was prepared in each of these examples and comparative examples by uniformly compounding: 12 parts of liquid paraffin, 3 parts of isopropyl palmitate, 3 parts of cetyl alcohol, 1.6 parts of glycerin monostearate, 1.5 parts of polyoxyethylene glycol monostearate, 5 parts of glycerin, a trace amount of a perfume, a trace amount of an antiseptic, 0.5 part of magnesium ellagate (Example 1), calcium ellagate (Example 2) or 2,2'-dihydroxy-4,4'-dimethoxy benzophenone (Comparative Example 1) and 73.4 parts (Examples 1 and 2 and Comparative Example 1) or 73.9 parts (Comparative Example 2) of purified water.

Each of the thus prepared cream preparations was applied to the skin of 6 animals a group of depilated guinea pigs symmetrically on the right and left back surfaces in a coating amount of 2 mg/cm$^2$ to prepare 6 slots on each animal and the thus coated slots were exposed to UV light from a UV lamp (Model FL-20-SE-30) for 0.5 minute, 1 minute, 2 minutes or 3 minutes. After 20 to 40 hours from the end of the UV exposure, the condition of the UV-irradiated skin of the animals was visually examined to record the degree of sunburn on each slot. The results are shown in Table 1 below by the numbers of the animals among six on which a clearly noticeable sunburn was found. For a control purpose, similar UV exposure tests were conducted for 6 animals uncoated with the cream preparations. The results of this control test are also shown in the same table.

As is clear from the results shown in the table, the cream preparations in Examples 1 and 2 exhibited a much higher anti-sunburn effect than the comparative cream preparations. Incidentally, the cream preparations were not responsible for irritative and allergic reactions according to the results of the safety check separately undertaken by the inventors.

TABLE 1

| Exposure time, minutes | Control | Example 1 | Example 2 | Comparative Example 1 | Comparative Example 2 |
|---|---|---|---|---|---|
| 0.5 | 0 | 0 | 0 | 0 | 0 |
| 1 | 2 | 0 | 0 | 1 | 1 |
| 2 | 6 | 1 | 1 | 3 | 6 |
| 3 | 6 | 1 | 2 | 6 | 6 |

Further, 20 women at the ages of 20s and 30s as the test members attended to a practical application tests of the cream preparations prepared in Examples 1 and 2 and Comparative Example 1 for the anti-sunburn effect by exposing their skin to the sunlight on a midsummer beach. The results are shown in Table 2 by the number of the test members among 20 who answered with satisfactory evaluation for the respective items.

The results shown in Table 2 clearly support the conclusion that the cream preparations according to the invention exhibited excellent performance in each of the test items of anti-sunburn effect, usability in respect of spreadability over the skin and absence of tackiness and condition of finishing as compared with the cream preparation in Comparative Example 1 which was definitely inferior in the anti-sunburn effect.

TABLE 2

| | Example 1 | Example 2 | Comparative Example 1 |
|---|---|---|---|
| Anti-sunburn effect | 17 | 16 | 6 |
| Spreadability over skin | 17 | 18 | 17 |
| Absence of tackiness | 18 | 18 | 16 |
| Condition of finishing | 17 | 18 | 10 |

EXAMPLE 3

A milky lotion was prepared by adding and emulsifying an oleaginous mixture composed of 2.0 parts of liquid paraffin, 1.0 part of cetyl alcohol, 1.0 part of stearic acid, 10 parts of isopropyl myristate, 0.7 part of polyoxyethylene glycol (20) stearyl ether, 0.5 part of glycerin monostearate and each a trace amount of a perfume, antiseptic and antioxidant in an aqueous mixture composed of 5.0 parts of 1,3-butylene glycol, 0.1 part of Carbopol 941, 0.5 part of calcium ellagate and water in an amount to make up 100 parts of the total amount of the oleaginous and aqueous mixtures each in a hot condition followed by cooling to room temperature.

EXAMPLE 4

A skin-care oil was prepared by successively adding and dissolving or dispersing 40 parts of olive oil, 0.5 part of barium ellagate and each a trace amount of a perfume and an antioxidant in 50.5 parts of liquid paraffin.

EXAMPLE 5

A face cream was prepared by admixing and compounding a oleaginous mixture composed of 5.0 parts of liquid paraffin, 10 parts of olive oil, 0.5 part of petrolatum, 3.0 parts of stearyl alcohol, 2.0 parts of stearic acid, 2.5 parts of sorbitan monostearate, 2.5 parts of polyoxyethylene sorbitan monostearate and each a trace amount of a perfume, antiseptic and antioxidant prepared with heating and an aqueous mixture composed of 5.0 parts of propylene glycol, 0.1 part of Carbopol, 1.0 part of magnesium ellagate, a trace amount of an antiseptic and water in an amount to make up 100 parts of the total amount of the oleaginous and aqueous mixtures followed by further addition of a small amount of a mixture of a coloring agent, dispersing aid, chelating agent and zinc oxide and cooling to room temperature.

EXAMPLE 6

A powdery foundation was prepared in the following manner. Thus, 10 parts of calcium ellagate, mica powder in an amount to make up 100 parts of the whole preparation, 15 parts of talc, 15 parts of titanium dioxide, 1.0 part of red iron oxide, 2.5 parts of yellow iron oxide and 0.1 part of black iron oxide were blended and finely pulverized and then transferred into a high-speed blender, in which the powdery blend was uniformly admixed with a uniform mixture of 7.0 parts of liquid paraffin, 2.0 parts of beeswax and each a trace amount of an antiseptic and perfume. The blend was again pulverized and, after screening to remove coarse particles, shaped by compression molding in a metal mold Into a form of a cake for compact.

EXAMPLE 7

A creamy foundation was prepared by adding and thoroughly dispersing a pulverized mixture of 8.0 parts of titanium dioxide, 7.0 parts of talc, 5.0 parts of magnesium ellagate and a small amount of a pigment in a solution of 1.2 parts of triethanol amine, 3.0 parts of sorbitol and trace amount of an antiseptic in water in an amount to make up 100 parts of the whole preparation. The dispersion heated at 70° C. was admixed with a mixture at 75° C. prepared from 5.0 parts of stearic acid, 2.0 parts of an oleophilic glycerin monostearate, 1.0 part of cetostearyl alcohol, 2.5 parts of propylene glycol monostearate, 5.0 parts of squalane and 5.0 parts of olive oil to give an emulsion. After cooling to 40° C., the emulsion was admixed with a trace amount of a perfume to give a creamy foundation.

What is claimed is:

1. An anti-sunburn skin-care preparation which comprises, as an effective ingredient for the absorption of ultraviolet lights, from 0.01 to 10% by weight of a polyvalent metal salt of an ellagic acid compound represented by the formula

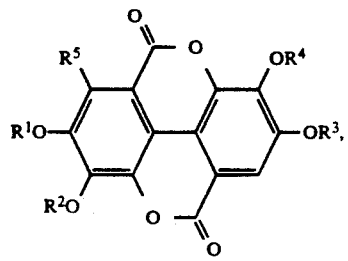

in which $R^1$, $R^2$, $R^3$ and $R^4$ are, each independently from the others, a hydrogen atom, an alkyl group having 1 to 20 carbon atoms, an acyl group having 1 to 20 carbon atoms, a polyoxyalkylene group of the formula

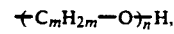

m being 2 or 3 and n being a positive integer, or a saccharide residue expressed by the formula

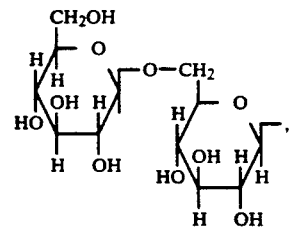

and $R^5$ is a hydrogen atom, a hydroxy group or an alkoxy group having 1 to 8 carbon atoms,
and a cosmetic carrier.

2. The anti-sunburn skin-care preparation as claimed in claim 1 wherein $R^1$, $R^2$, $R^3$, $R^4$ and $R^5$ are each a hydrogen atom.

3. The anti-sunburn skin-care preparation as claimed in claim 1 wherein the polyvalent metal is selected from the group consisting of copper, calcium, strontium, barium, magnesium, zinc, aluminum, titanium, zirconium, iron and cobalt 4. The anti-sunburn skin-care preparation as claimed in claim 3, wherein the preferred polyvalent metal salt is selected from the group consisting of calcium, magnesium and barium.

5. A skin-care cream composition comprising the anti-sunburn preparation according to claim 1.

6. A skin care lotion composition comprising the anti-sunburn preparation according to claim 1.

7. A method for protecting human skin from sunburn by exposure to ultraviolet light which comprises applying, to the human skin, an effective amount of an anti-sunburn skin-care preparation comprising, as an effective ingredient for the absorption of ultraviolet light, from 0.01 to 10% by weight of a polyvalent metal salt of an ellagic acid compound represented by the formula

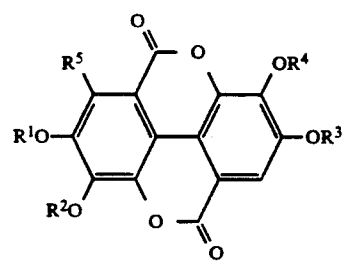

in which $R^1$, $R^2$, $R^3$ and $R^4$ are, each independently from the others, a hydrogen atom, an alkyl group having 1 to 20 carbon atoms, an acyl group having 1 to 20 carbon atoms, a polyoxyalkylene group of the formula

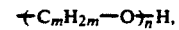

m being 2 or 3 and n being a positive integer, or a saccharide residue expressed by the formula

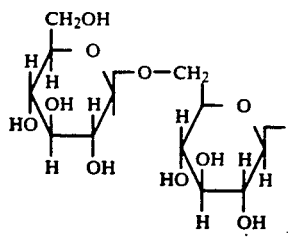

and $R^5$ is a hydrogen atom, a hydroxy group or an alkoxy group having 1 to 8 carbon atoms, and a cosmetic carrier.

8. The method of claim 7, wherein the polyvalent metal is selected from the group consisting of copper, calcium, strontium, barium, magnesium, zinc, aluminum, titanium, zirconium, iron and cobalt.

9. The method of claim 8, wherein the preferred polyvalent metal is selected from the group consisting of calcium, magnesium, and barium.

* * * * *